(12) United States Patent
Engelbart et al.

(10) Patent No.: US 8,583,271 B2
(45) Date of Patent: Nov. 12, 2013

(54) CONTROLLING CUTTING OF CONTINUOUSLY FABRICATED COMPOSITE PARTS WITH NONDESTRUCTIVE EVALUATION

(75) Inventors: Roger W. Engelbart, Webster Groves, MO (US); Steven J. Burpo, Saint Charles, MO (US); Michael P. Renieri, Marthasville, MO (US)

(73) Assignee: The Boeing Company, Chicago, IL (US)

( * ) Notice: Subject to any disclaimer, the term of this patent is extended or adjusted under 35 U.S.C. 154(b) by 825 days.

(21) Appl. No.: 12/404,453

(22) Filed: Mar. 16, 2009

(65) Prior Publication Data

US 2010/0234977 A1 Sep. 16, 2010

(51) Int. Cl.
*B23P 11/02* (2006.01)
*G05B 19/18* (2006.01)
*G06F 19/00* (2011.01)
*B23K 26/00* (2006.01)
*G05B 13/02* (2006.01)

(52) U.S. Cl.
USPC .......... 700/110; 700/63; 700/98; 219/121.67; 29/448; 702/36

(58) Field of Classification Search
None
See application file for complete search history.

(56) References Cited

U.S. PATENT DOCUMENTS

| | | | |
|---|---|---|---|
| 5,408,882 A * | 4/1995 | McKinley et al. | 73/597 |
| 5,659,479 A * | 8/1997 | Duley et al. | 700/166 |
| 6,122,564 A * | 9/2000 | Koch et al. | 700/123 |
| 6,757,006 B1 * | 6/2004 | Yabe | 348/86 |
| 6,868,883 B2 * | 3/2005 | Benedetti | 156/353 |
| 7,193,696 B2 | 3/2007 | Engelbart et al. | |
| 7,841,264 B2 * | 11/2010 | Kim et al. | 83/13 |
| 7,951,258 B2 * | 5/2011 | Karlsson et al. | 156/291 |
| 2005/0021280 A1 * | 1/2005 | Woods et al. | 702/142 |
| 2005/0137740 A1 * | 6/2005 | Lindstrom et al. | 700/182 |
| 2007/0204555 A1 | 9/2007 | Engelbart et al. | |
| 2008/0141777 A1 | 6/2008 | Engelbart et al. | |
| 2012/0093391 A1 | 4/2012 | Engelbart et al. | |

OTHER PUBLICATIONS

Hsu, David K., "Non-destructive Inspection of Composite Structures: Methods and Practise", 17th World Conference on NonDestructive Testing, Shanghai, China, Oct. 25, 2008.*

Hsu, David, "NonDestructive Inspection of Composite Structures: Methods and Practice", 17th World Conference on Nondestructive Testing, Oct. 25-28, 2008, Shanghai, China, http://www.ndt.net/article/wcndt2008/toc.htm, pp. 1-14.*

Hsu, David, "NonDestructive Inspection of Composite Structures: Methods and Practise", 17th World Conference on Nondestructive Testing, Oct. 25-28, 2008, Shanghai, China, Http://www.ndt.net/article/wcndt2008/toc.htm, pp. 1-14.*

(Continued)

*Primary Examiner* — Kakali Chaki
*Assistant Examiner* — Walter Hanchak
(74) *Attorney, Agent, or Firm* — Yee & Associates, P.C.

(57) ABSTRACT

An apparatus may comprise a nondestructive evaluation system and a cutting system. The nondestructive evaluation system may be configured to inspect a processed portion of a structure. The nondestructive evaluation system may be configured to determine whether an inconsistency is present in the processed portion. The nondestructive evaluation system may also be configured to generate information about a location of the inconsistency. The cutting system may be configured to cut a number of parts out of the processed portion of the structure in which the inconsistency may be at least substantially excluded from the number of parts.

24 Claims, 5 Drawing Sheets

(56) References Cited

OTHER PUBLICATIONS

MIL-HDBK-17-3F "Department of Defense Handbook, Composite Materials Handbook, vol. 3, Polymer Matrix Composites Materials Usage, Design and Analysis", Department of Defense, vol. 3 of 5, Jun. 17, 2002.* sampe.org, "SAMPE '08 Conference Program and Exhibitor's Guide", sampe.org, "http://www.sampe.org/events/LongBeach08FinalProgram.pdf", May 22, 2008, pp. 1-60.* ibm staff, "Engineering Solutions Application Portfolio: from design to prodict-in-operation", IBM, "http://www.cad-cam-data.com/plm/pdf/CATIAV4.pdf", 1999, pp. 1-36.*

U.S. Appl. No. 12/103,178, filed Apr. 15, 2008, Engelbart et al.

* cited by examiner

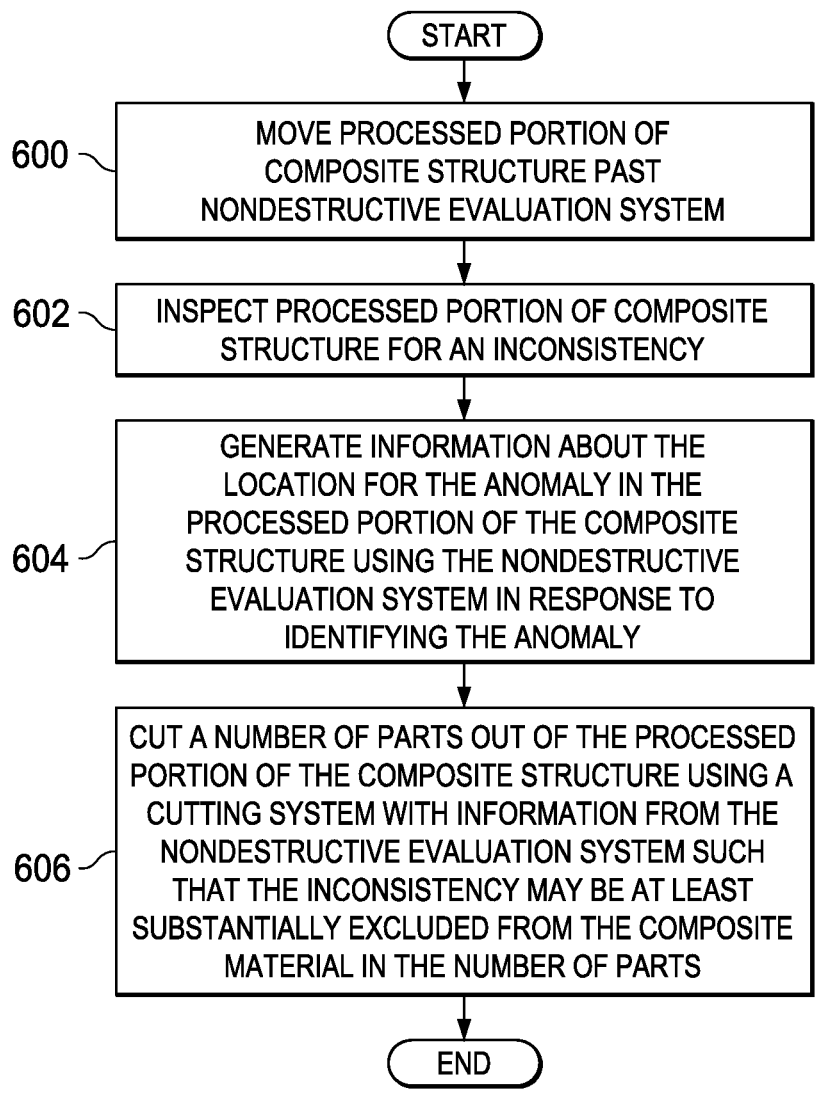

CONTROLLING CUTTING OF CONTINUOUSLY FABRICATED COMPOSITE PARTS WITH NONDESTRUCTIVE EVALUATION

BACKGROUND INFORMATION

1. Field

The present disclosure relates generally to manufacturing and, in particular, to a method and apparatus for continuously fabricating composite structures. Still more particularly, the present disclosure relates to a method and apparatus for cutting continuously fabricated composite structures.

2. Background

In manufacturing parts, continuous fabrication systems may be employed to fabricate parts from composite structures. For example, a continuous fabrication system may manufacture a composite structure having a first face sheet and a second face sheet with a core sandwiched between the two fiberglass sheets. As another example, the continuous fabrication system may manufacture the face sheets with carbon sheets instead of fiberglass sheets.

This composite structure may be continuously manufactured in a continuous fabrication system. For example, the composite structure may be fed through the continuous fabrication system. The continuous fabrication system may apply pressure and/or heat to the composite structure to cause the components to cure, bond, attach, and/or adhere to each other. The structure output from the continuous fabrication system may be a processed composite structure.

As a result, the composite structure may be fabricated continuously. For example, without limitation, a completed composite structure may exit the continuous fabrication system, while an uncured and/or unprocessed portion of the composite structure enters the continuous fabrication system for processing.

Parts may be cut out of the processed portion of the composite structure. For example, without limitation, these types of composite structures may be used for floorboards on aircraft, truck cabs, and/or other suitable vehicles. These composite structures also may be used to fabricate other types of parts such as, for example, without limitation, floor beams, longerons, stringers, ribs, skin panels, and other suitable types of parts.

Typically, after the parts are formed from the composite structure, the parts may be inspected to identify inconsistencies. If an inconsistency is present within the part, a determination may be made as to whether the part can be reworked or may be discarded.

This type of manufacturing environment may result in three discreet steps. One step may involve manufacturing the composite structure. A second step may involve cutting parts out of the composite structure, and a third step may involve inspecting the composite structure.

This type of fabrication of parts, however, may result in an increase in the cost of parts when inconsistencies are found and parts are discarded. Further, if the part with the inconsistency can be reworked, the amount of time needed to manufacture the part may be increased.

Therefore, it would be advantageous to have a method and apparatus that takes into account one or more of the issues discussed above, as well as possibly other issues.

SUMMARY

In one advantageous embodiment, an apparatus may comprise a nondestructive evaluation system and a cutting system. The nondestructive evaluation system may be configured to inspect a processed portion of a structure. The nondestructive evaluation system may be configured to determine whether an inconsistency is present in the processed portion. The nondestructive evaluation system may also be configured to generate information about a location of the inconsistency. The cutting system may be configured to cut a number of parts out of the processed portion of the structure in which the inconsistency may be at least substantially excluded from the number of parts.

In another advantageous embodiment, an aircraft part manufacturing apparatus may comprise a continuous manufacturing system, a nondestructive evaluation system, a cutting system, a computer system, a transformation process, and a control process. The continuous manufacturing system may be configured to process an unprocessed portion of a composite structure to form a processed portion of the composite structure having a continuous cross section. The nondestructive evaluation system may be configured to inspect the processed portion of the composite structure. The nondestructive evaluation system may be configured to determine whether an inconsistency is present in the processed portion and/or identify a presence of the inconsistency in the processed portion of the composite structure. The nondestructive evaluation system may also be configured to generate information about a location of the inconsistency in response to identifying the presence of the inconsistency. The nondestructive evaluation system may be an ultrasound system. The cutting system may be configured to cut a number of aircraft parts out of the processed portion of the composite structure, in which the inconsistency may be substantially excluded from the number of aircraft parts. The cutting system may comprise at least one of a laser cutter and a circular blade. The computer system may be configured to control the nondestructive evaluation system and the cutting system. The transformation process may be configured to execute on the computer system. The transformation process may be configured to transform the information from a first format generated by the nondestructive evaluation system into a second format used by the control process to identify a number of shapes for the number of aircraft parts to cut out of the processed portion of the composite structure using the information, such that the inconsistency may be substantially excluded from the number of aircraft parts. The control process may be configured to execute on the computer system to identify the number of shapes for the number of aircraft parts to cut out of the processed portion of the composite structure using a first computer-aided design model in the second format for the number of aircraft parts and the information in the second format such that the inconsistency may be substantially excluded from the number of aircraft parts. The control process may be configured to identify the number of shapes using a model in the second format for the number of aircraft parts and receive the information in the second format.

In yet another advantageous embodiment, a method may be present for processing a composite structure. A processed portion of the composite structure may be moved past a nondestructive evaluation system. The processed portion of the composite structure may be inspected for an inconsistency. The inconsistency may be identified. Information about the location for the inconsistency in the processed portion of the composite structure may be generated using the nondestructive evaluation system in response to identifying the inconsistency. At least one part may be cut out of the processed portion of the composite structure using a cutting system with the information from the nondestructive evaluation system. The inconsistency may be substantially excluded from the composite structure in the number of parts.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives, and advantages thereof, will best be understood by reference to the following detailed description of an advantageous embodiment of the present disclosure when read in conjunction with the accompanying drawings, wherein:

FIG. 6 is an illustration of a flowchart of a process for processing a structure in accordance with an advantageous embodiment.

DETAILED DESCRIPTION

Figure 1:
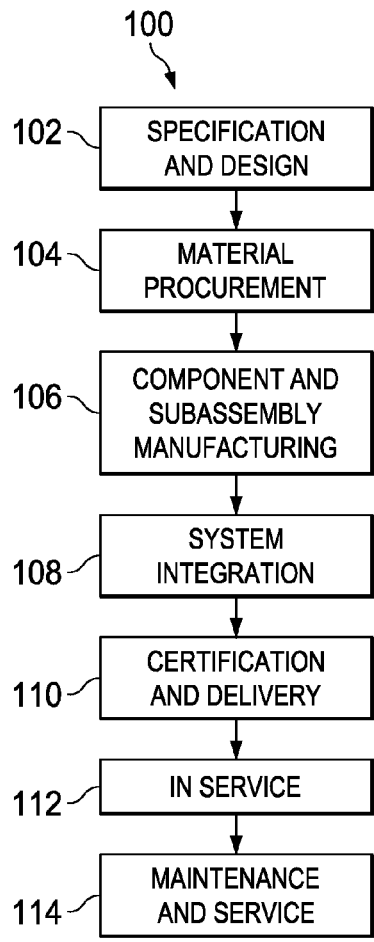
FIG. 1 is an illustration of an aircraft manufacturing and service method in accordance with an advantageous embodiment.
Figure 2:
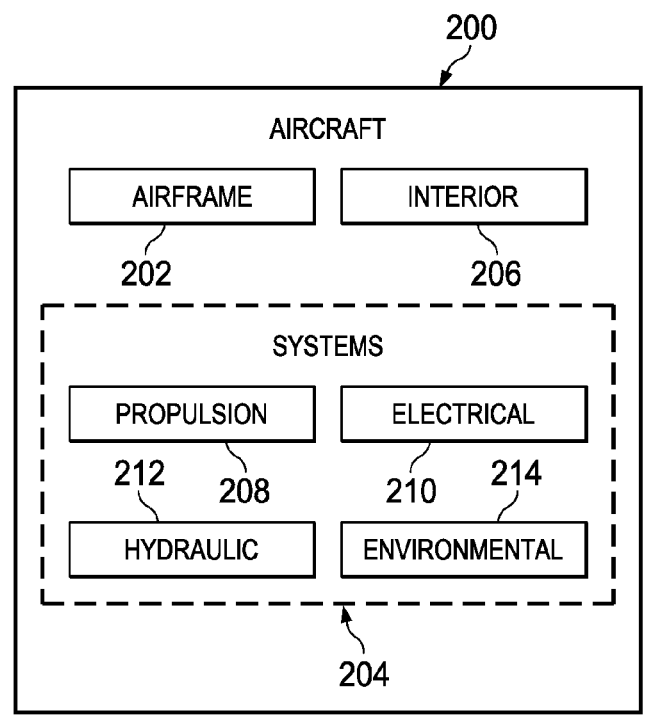
FIG. 2 is an illustration of an aircraft in which an advantageous embodiment may be implemented.

Referring more particularly to the drawings, embodiments of the disclosure may be described in the context of aircraft manufacturing and service method 100 as shown in FIG. 1 and aircraft 200 as shown in FIG. 2. Turning first to FIG. 1, an illustration of an aircraft manufacturing and service method is depicted in accordance with an advantageous embodiment. During pre-production, exemplary aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of venders, subcontractors, and suppliers; and an operator may be an airline, leasing company, military entity, service organization, and so on.

With reference now to FIG. 2, an illustration of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion system 208, electrical system 210, hydraulic system 212, and environmental system 214. Any number of other systems may be included. Although an aerospace example is shown, different advantageous embodiments may be applied to other industries, such as the automotive industry.

Apparatus and methods embodied herein may be employed during any one or more of the stages of aircraft manufacturing and service method 100 in FIG. 1. For example, components or subassemblies produced in component and subassembly manufacturing 106 in FIG. 1 may be fabricated or manufactured in a manner similar to components or subassemblies produced while aircraft 200 is in service 112 in FIG. 1.

Also, one or more apparatus embodiments, method embodiments, or a combination thereof may be utilized during production stages, such as component and subassembly manufacturing 106 and system integration 108 in FIG. 1, for example, without limitation, by substantially expediting the assembly of or reducing the cost of aircraft 200. Similarly, one or more of apparatus embodiments, method embodiments, or a combination thereof may be utilized while aircraft 200 is in service 112 or during maintenance and service 114 in FIG. 1.

As a specific example, one or more of the different advantageous embodiments may be implemented in component and subassembly manufacturing 106 to produce parts for aircraft 200. Additionally, one or more advantageous embodiments also may be employed during maintenance and service 114 to fabricate parts for aircraft 200. These parts may be replacement parts and/or upgrade parts.

The different advantageous embodiments recognize and take into account a number of different considerations. For example, the different advantageous embodiments recognize and take into account that during the fabrication of composite parts, it may be necessary to cut out or cut around an inconsistency in the composite material. This type of operation may be part of the rework of a composite structure.

The different advantageous embodiments recognize and take into account that this type of approach may be more efficient for fabrication and more cost efficient than allowing the inconsistency to remain. The different advantageous embodiments also recognize and take into account that continuous fabrication processes may be employed. The different advantageous embodiments also recognize and take into account that these processes may include a cutting system that cuts a composite structure into sections for use.

Further, the different advantageous embodiments recognize and take into account that additional cutting may be used to perform a final trim of the part, remove areas with inconsistencies. The different advantageous embodiments recognize and take into account that this type of final cutting may be performed using, for example, without limitation, a robotic water jet cutting machine that may perform more complex trimming and cutting.

Further, the different advantageous embodiments recognize and take into account that the processes to control the production of composite parts from composite structures may involve nesting routines. The different advantageous embodiments recognize and take into account that currently, anticipating locations with inconsistencies and preparing nesting routines in advance to remove these inconsistencies are not available operations.

The different advantageous embodiments recognize and take into account that the current processes for fabricating parts perform a post-manufacturing evaluation operation to determine whether inconsistencies may be present. The locations of inconsistencies may be physically marked and/or outlined on the surface of the composite structure for the part. These locations also may be compared to a model to identify coordinates on the part. These coordinates may then be used to develop a nesting routine to cut out the inconsistency.

The different advantageous embodiments recognize and take into account that the existing solution requires multiple steps and requires manual marking and measurement to create the data needed to create a nesting routine after the inspection has been performed. The different advantageous embodiments recognize and take into account that the cutting operation may be delayed until these steps are completed.

Thus, the different advantageous embodiments provide a method and apparatus for processing a structure. The structure may be, for example, without limitation, a composite structure from which parts may be cut. The apparatus may comprise a nondestructive evaluation system and a cutting system. The nondestructive evaluation system may be configured to inspect a portion of the structure moving through the nondestructive evaluation system, determine whether an inconsistency is present in the portion, and generate information about a location of the inconsistency.

The cutting system may be configured to cut a number of parts out of the processed portion of the structure in which the inconsistency may be at least substantially excluded from the number of parts. An inconsistency may be substantially excluded from a part if the part still meets the requirements for use when a portion of the inconsistency is present in the part.

Figure 3:
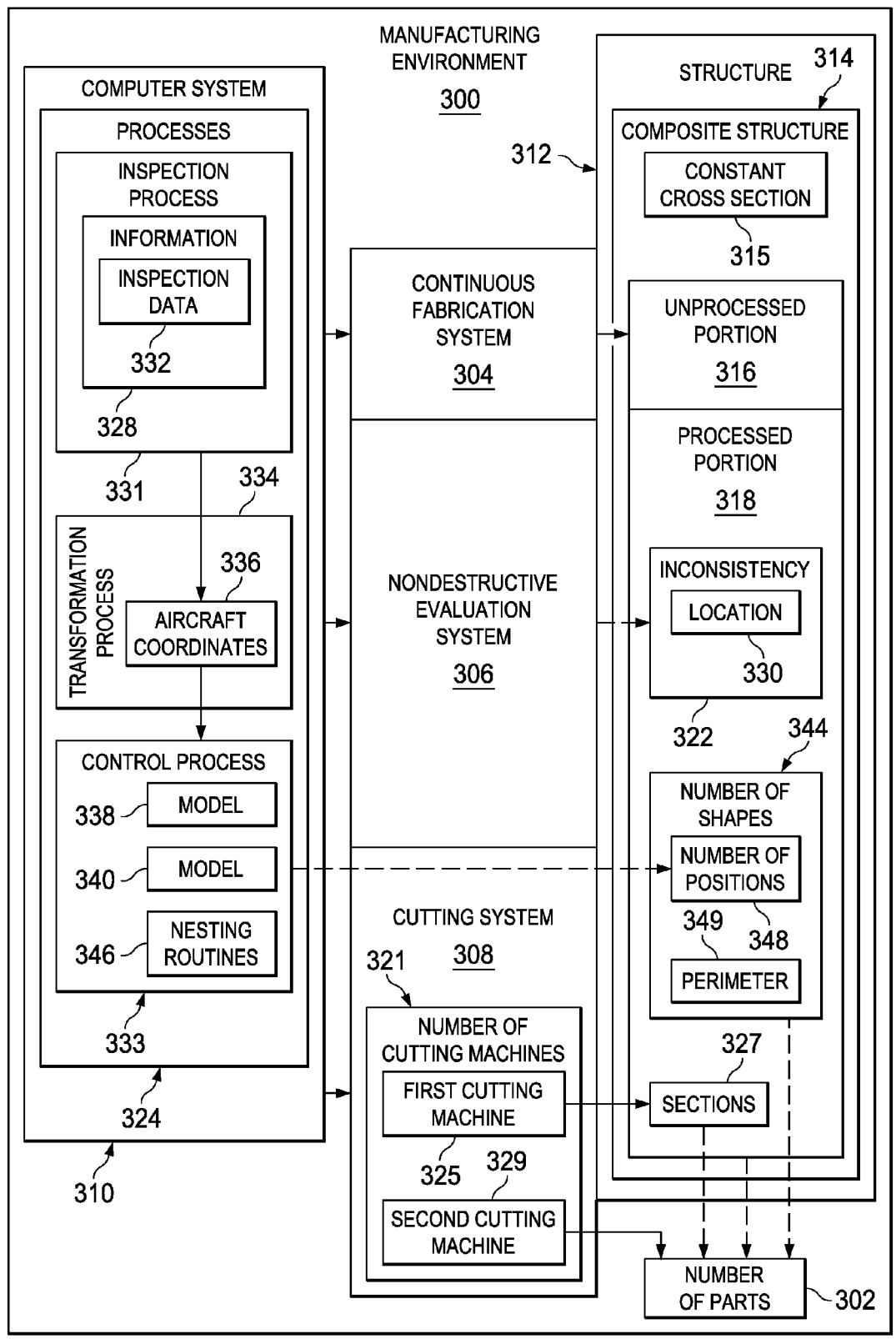
FIG. 3 is an illustration of a manufacturing environment in accordance with an advantageous embodiment.

With reference now to FIG. 3, an illustration of a manufacturing environment is depicted in accordance with an advantageous embodiment. Manufacturing environment 300 may be used to manufacture number of parts 302 for aircraft 200 in FIG. 2.

In this illustrative example, manufacturing environment 300 includes continuous fabrication system 304, nondestructive evaluation system 306, cutting system 308, and computer system 310.

Continuous fabrication system 304 may fabricate structure 312. In these illustrative examples, structure 312 takes the form of composite structure 314. Composite structure 314 may be formed from raw materials. Composite structure 314 may have two or more different types of raw materials and/or may have the same types of raw material in different forms. Of course, in other advantageous embodiments, structure 312 may be a homogeneous structure such as, for example, without limitation, fiberglass.

In these illustrative examples, continuous fabrication system 304 may be used to fabricate composite structure 314 using any process capable of manufacturing composite structure 314 with constant cross section 315. Composite structure 314 may have any length, depending on the particular implementation. Continuous fabrication system 304 may manufacture composite structure 314 using a number of different types of processes. For example, without limitation, continuous fabrication system 304 may use continuous resin transfer molding, pultrusion, continuous compression molding, and/or some other suitable type of fabrication process.

Continuous fabrication system 304 may be implemented using any currently available continuous manufacturing system. For example, without limitation, continuous fabrication system 304 may be implemented using a P100 or P50 Pultrusion Machine available from Entec Composite Machines, Inc. As another example, a continuous resin transfer molding machine may be available from Glasforms, Inc. to implement continuous fabrication system 304.

In these illustrative examples, unprocessed portion 316 of composite structure 314 enters continuous fabrication system 304. Unprocessed portion 316 may be raw materials laid up for composite structure 314. Raw materials, in these illustrative examples, may be uncured materials. These raw materials may include, for example, without limitation, fiber, resin, forms, tape, and/or other suitable materials. Processed portion 318 of composite structure 314 exits continuous fabrication system 304. Processed portion 318 may contain cured materials. Processed portion 318 may be in a condition ready for inspection by nondestructive evaluation system 306 and for cutting by cutting system 308.

In the illustrative examples, processed portion 318 may move through nondestructive evaluation system 306. Nondestructive evaluation system 306 may inspect processed portion 318 to determine whether inconsistency 322 is present in processed portion 318. Inconsistency 322 may be an area and/or volume in portion 318 that is out of a design tolerance and/or standard. In these illustrative examples, inconsistency 322 may be, for example, without limitation, a foreign material, a delamination, a void, a porosity level out of tolerance, and/or some other type of inconsistency.

Nondestructive evaluation system 306 may be implemented using any nondestructive evaluation system capable of providing inspection data, while composite structure 314 is manufactured by continuous fabrication system 304.

In these illustrative examples, nondestructive evaluation system 306 may take a number of different forms. For example, without limitation, nondestructive evaluation system 306 may be an ultrasonic system, a coordinate measuring machine, a laser tracker, and/or some other suitable type of nondestructive evaluation system. Nondestructive evaluation system 306 may be implemented using any currently available nondestructive evaluation system. For example, without limitation, nondestructive evaluation system 306 may be implemented using an automated mobile ultrasonic scanning system, AUSS V, which is available from the Boeing Company.

In these depicted examples, cutting system 308 cuts number of parts 302 out of processed portion 318 of composite structure 314. Cutting system 308 may comprise number of cutting machines 321. For example, without limitation, number of cutting machines 321 may be at least one of a laser cutter, a circular saw machine, and/or some other type of cutting machine.

In some advantageous embodiments, a single cutting machine may cut number of parts 302 out of processed portion 318. In other advantageous embodiments, first cutting machine 325 may cut sections 327 out of processed portion 318 of composite structure 314. Second cutting machine 329 may cut number of parts 302 out of sections 327. In other advantageous embodiments, number of parts 302 may be cut directly out of processed portion 318 in composite structure 314 without cutting sections 327.

In these illustrative examples, cutting system 308 may take a number of different forms. For example, without limitation, cutting system 308 may be a robotic cutting system that may use a laser and/or circular blade to cut out number of parts 302. Cutting system 308 may be, for example, without limitation, a model 61L Evolution Laser System, which may be available from Precix Advanced Cutting Technologies, Inc.

In the depicted examples, computer system 310 is a number of computers. A number, as used herein, with reference to an item, means one or more items. For example, a number of computers is one or more computers. Computer system 310 may control continuous fabrication system 304, nondestructive evaluation system 306, and cutting system 308 in these illustrative examples. In these examples, computer system 310 may execute processes 324. Processes 324 may include inspection process 331. Inspection process 331 may control nondestructive evaluation system 306 to identify inconsistency 322.

If nondestructive evaluation system 306 may identify inconsistency 322 in processed portion 318, nondestructive evaluation system 306 may generate information 328 about location 330 of inconsistency 322. Information 328 also may include other information about inconsistency 322. For example, without limitation, information 328 also may include the size and/or shape of inconsistency 322. Information 328 may be formatted to control cutting system 308. Information 328, in these illustrative examples, may take the form of inspection data 332 in a format for nondestructive evaluation system 306.

Transformation process 334 in processes 324 may receive inspection data 332 and may transform inspection data 332 into aircraft coordinates 336. Aircraft coordinates 336 may be in a format that is capable of being used by control process 333 in processes 334 to cut number of parts 302 out of processed portion 318 of composite structure 314.

For example, inspection data 332 may be transformed by transformation process 334 into aircraft coordinates 336. Aircraft coordinates 336 may be placed into model 338 for inconsistency 322. Model 338 may be used with model 340 for number of parts 302 to identify number of shapes 344 on processed portion 318 of composite structure 314. These models may be, for example, without limitation, a computer-aided design model.

Computer system 310 executes control process 333. In these examples, control process 333 may include nesting routines 346. In these illustrative examples, nesting routines 346 may be a number of software subroutines that continuously run and update number of shapes 344 for cutting out number of parts 302 on processed portion 318.

Nesting routines 346 may maximize number of parts 302 that may be cut out of processed portion 318. In other words, nesting routines 346 and control process 333 may maximize the density of number of parts 302 that can be cut out of processed portion 318.

In these illustrative examples, nesting routines 346 use model 340 for number of parts 302. Model 340 identifies number of shapes 344 that may be located in processed portion 318 and cut out to form number of parts 302. Further, with model 338 containing information 328 about location 330 for inconsistency 322, nesting routines 346 in control process 333 may select number of positions 348 for number of shapes 344 in a manner that perimeter 349 for number of shapes 344 at least substantially excludes inconsistency 322.

In some advantageous embodiments, number of positions 348 for number of shapes 344 may be selected such that inconsistency 322 may be substantially excluded from number of parts 302. In this manner, nesting routines 346 in control process 333 may control cutting system 308 to cut out number of parts 302 from processed portion 318 in a manner such that inconsistency 322 is located systematically outside of number of parts 302.

In these illustrative examples, control process 333 may update nesting routines 346 as inconsistencies are identified, such that number of parts 302 may be cut out of processed portion 318 without delays.

The control of cutting system 308 by computer system 310 may occur, while composite structure 314 continues to be manufactured. In other words, processed portion 318 may be continuously produced from unprocessed portion 316 by continuous fabrication system 304, while nondestructive evaluation system 306 may perform nondestructive testing of processed portion 318.

Further, cutting of number of parts 302 by cutting system 308 in a manner that systematically excludes inconsistency 322 from number of parts 302 may occur as continuous fabrication system 304 manufactures processed portion 318 from unprocessed portion 316 of composite structure 314. In other words, processed portion 318 may move through nondestructive evaluation system 306 to cutting system 308 for processing into number of parts 302.

In this illustrative example, the fabrication of processed portion 318, the inspection of processed portion 318, and the cutting of processed portion 318 may be performed as a single process without delays. In other words, the manufacturing, inspection, and cutting of processed portion 318 may occur without having to halt and/or slow down the fabrication of processed portion 318 by continuous fabrication system 304.

The illustration of manufacturing environment 300 in FIG. 3 is not meant to imply physical or architectural limitations to the manner in which different advantageous embodiments may be implemented. Other components in addition to and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

For example, in some advantageous embodiments, computer system 310 may be part of continuous fabrication system 304, nondestructive evaluation system 306, and/or cutting system 308. With this type of implementation, computer system 310 may not be a separate functional component as illustrated in FIG. 3. Instead, the different processes and functionalities may be integrated within the other systems. For example, computer system 310 may be integrated into or part of at least one of continuous fabrication system 304, nondestructive evaluation system 306, cutting system 308, and/or some other suitable system in manufacturing environment 300.

In still other examples, additional inconsistencies in addition to inconsistency 322 may be detected by nondestructive evaluation system 306. Nesting routines 346 may adjust number of shapes 344 in a manner that increases number of parts 302 in processed portion 318 without inconsistencies.

In some advantageous embodiments, inconsistency 322 may be substantially excluded from the composite structure. For example, all of inconsistency 322 may be out of tolerance if included in number of parts 302. However, if a portion of inconsistency 322 is present in number of parts 302, that portion of inconsistency 322 may be within the design tolerance. As a result, in some advantageous embodiments, all of inconsistency 322 or all of the inconsistencies may not need to be outside of number of shapes 344 for number of parts 302. Of course, in some advantageous embodiments, the design tolerances may require all of inconsistency 322 to be left outside of number of parts 302 when adjusting number of shapes 344.

Of course, depending on the size of inconsistency 322 and whether other inconsistencies may be present, nesting routines 346 may adjust number of shapes 344 such that various parts of processed portion 318 may be unused for number of parts 302. If inconsistency 322 is large enough and/or other inconsistencies are present, it is possible that processed portion 318 may not be used at all. In this situation, new materials may need to be obtained and the manufacturing of composite structure 314 may have to be restarted.

Figure 4:
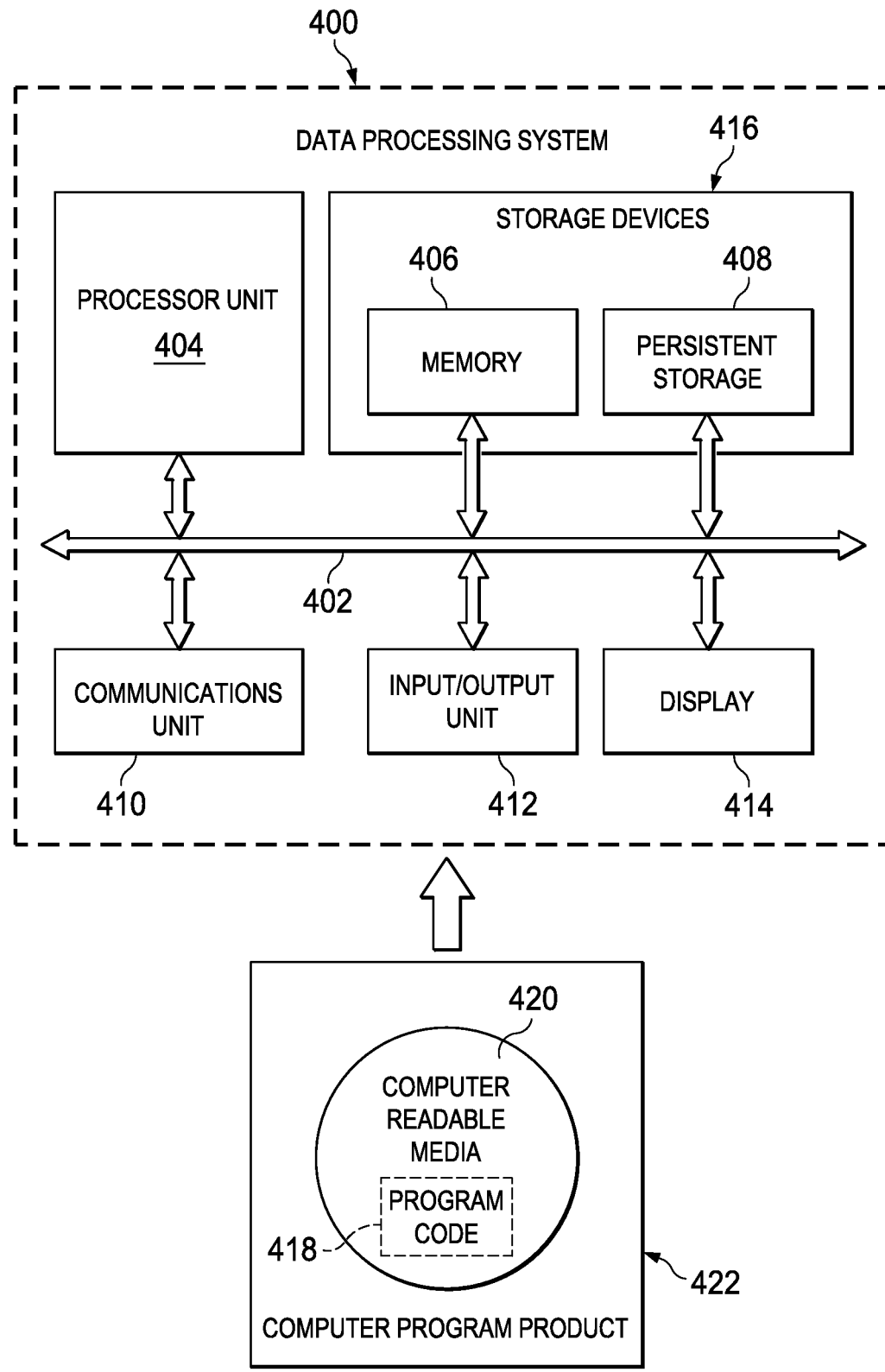
FIG. 4 is an illustration of a data processing system in accordance with an advantageous embodiment.

Turning now to FIG. 4, an illustration of a data processing system is depicted in accordance with an advantageous embodiment. In this illustrative example, data processing system 400 includes communications fabric 402, which provides communications between processor unit 404, memory 406, persistent storage 408, communications unit 410, input/output (I/O) unit 412, and display 414. Data processing system 400 is an example of a data processing system that may be used to implement one or more computers in computer system 310 in FIG. 3.

Processor unit 404 serves to execute instructions for software that may be loaded into memory 406. Processor unit 404 may be a set of one or more processors or may be a multi-processor core, depending on the particular implementation. Further, processor unit 404 may be implemented using one or more heterogeneous processor systems in which a main processor is present with secondary processors on a single chip. As another illustrative example, processor unit 404 may be a symmetric multi-processor system containing multiple processors of the same type.

Memory 406 and persistent storage 408 are examples of storage devices 416. A storage device is any piece of hardware that is capable of storing information such as, for example, without limitation, data, program code in functional form, and/or other suitable information either on a temporary basis and/or a permanent basis. Memory 406, in these examples, may be, for example, without limitation, a random access memory or any other suitable volatile or non-volatile storage device.

Persistent storage 408 may take various forms, depending on the particular implementation. For example, persistent storage 408 may contain one or more components or devices. For example, persistent storage 408 may be a hard drive, a flash memory, a rewritable optical disk, a rewritable magnetic tape, or some combination of the above. The media used by persistent storage 408 also may be removable. For example, a removable hard drive may be used for persistent storage 408.

Communications unit 410, in these examples, provides for communications with other data processing systems or devices. In these examples, communications unit 410 is a network interface card. Communications unit 410 may provide communications through the use of either or both physical and wireless communications links.

Input/output unit 412 allows for input and output of data with other devices that may be connected to data processing system 400. For example, input/output unit 412 may provide a connection for user input through a keyboard, a mouse, and/or some other suitable input device. Further, input/output unit 412 may send output to a printer. Display 414 provides a mechanism to display information to a user.

Instructions for the operating system, applications, and/or programs may be located in storage devices 416, which are in communication with processor unit 404 through communications fabric 402. In these illustrative examples, the instructions are in a functional form on persistent storage 408. These instructions may be loaded into memory 406 for execution by processor unit 404. The processes of the different embodiments may be performed by processor unit 404 using computer-implemented instructions, which may be located in a memory, such as memory 406.

These instructions are referred to as program code, computer usable program code, or computer readable program code that may be read and executed by a processor in processor unit 404. The program code in the different embodiments may be embodied on different physical or tangible computer readable media, such as memory 406 or persistent storage 408.

Program code 418 is located in a functional form on computer readable media 420 that is selectively removable and may be loaded onto or transferred to data processing system 400 for execution by processor unit 404. Program code 418 and computer readable media 420 form computer program product 422 in these examples. In one example, computer readable media 420 may be in a tangible form such as, for example, an optical or magnetic disk that is inserted or placed into a drive or other device that is part of persistent storage 408 for transfer onto a storage device, such as a hard drive that is part of persistent storage 408.

In a tangible form, computer readable media 420 also may take the form of a persistent storage, such as a hard drive, a thumb drive, or a flash memory that is connected to data processing system 400. The tangible form of computer readable media 420 is also referred to as computer recordable storage media. In some instances, computer readable media 420 may not be removable.

Alternatively, program code 418 may be transferred to data processing system 400 from computer readable media 420 through a communications link to communications unit 410 and/or through a connection to input/output unit 412. The communications link and/or the connection may be physical or wireless in the illustrative examples. The computer readable media also may take the form of non-tangible media, such as communications links or wireless transmissions containing the program code.

In some illustrative embodiments, program code 418 may be downloaded over a network to persistent storage 408 from another device or data processing system for use within data processing system 400. For instance, program code stored in a computer readable storage medium in a server data processing system may be downloaded over a network from the server to data processing system 400. The data processing system providing program code 418 may be a server computer, a client computer, or some other device capable of storing and transmitting program code 418.

The different components illustrated for data processing system 400 are not meant to provide architectural limitations to the manner in which different embodiments may be implemented. The different illustrative embodiments may be implemented in a data processing system including components in addition to or in place of those illustrated for data processing system 400.

Other components shown in FIG. 4 can be varied from the illustrative examples shown. The different embodiments may be implemented using any hardware device or system capable of executing program code. As one example, the data processing system may include organic components integrated with inorganic components and/or may be comprised entirely of organic components excluding a human being. For example, a storage device may be comprised of an organic semiconductor.

As another example, a storage device in data processing system 400 is any hardware apparatus that may store data. Memory 406, persistent storage 408, and computer readable media 420 are examples of storage devices in a tangible form.

In another example, a bus system may be used to implement communications fabric 402 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 406 or a cache such as found in an interface and memory controller hub that may be present in communications fabric 402.

Figure 5:
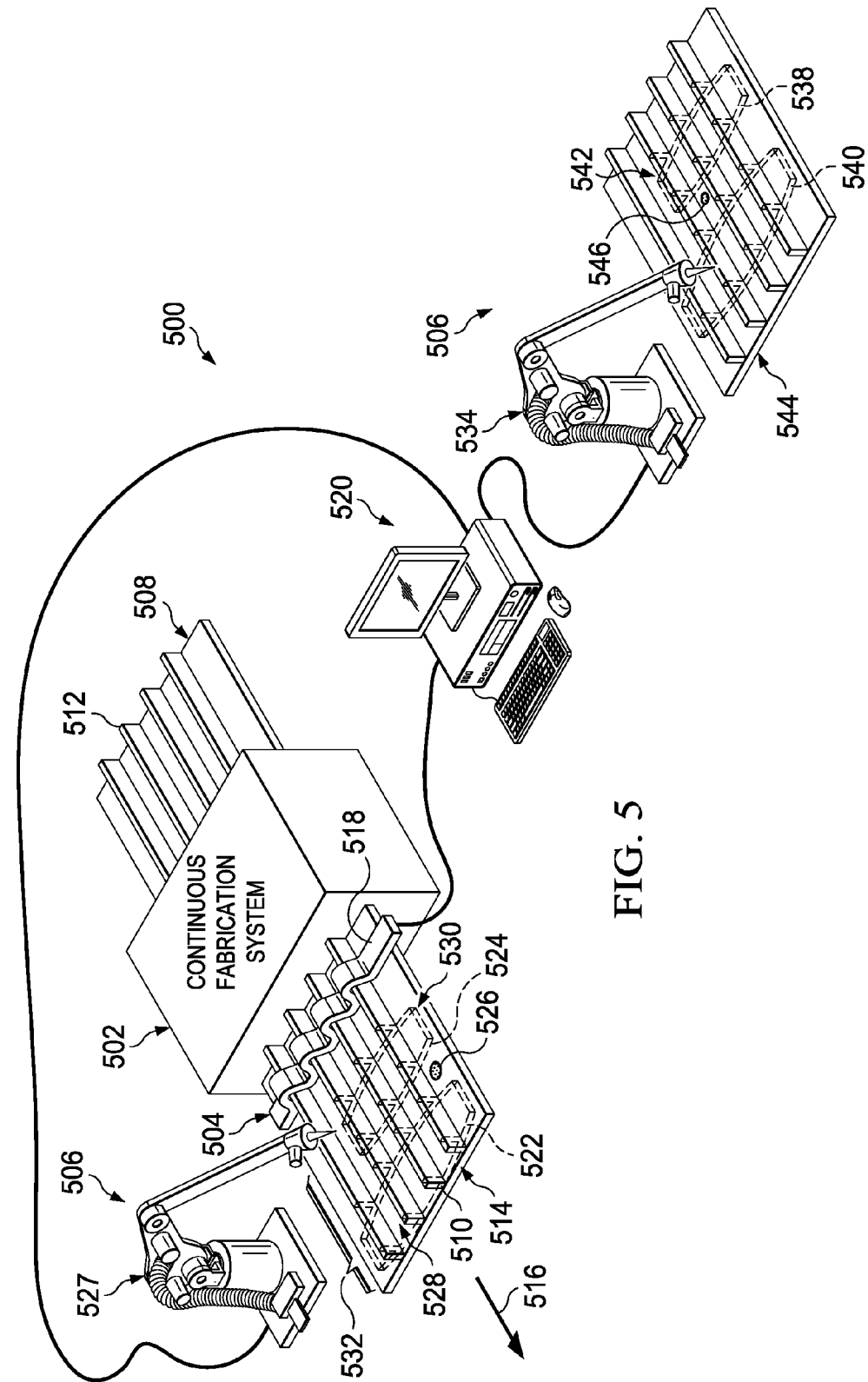
FIG. 5 is an illustration of a manufacturing environment in accordance with an advantageous embodiment.

Turning now to FIG. 5, an illustration of a manufacturing environment is depicted in accordance with an advantageous embodiment. In this illustrative example, manufacturing environment 500 may be an example of one implementation for manufacturing environment 300 in FIG. 3. In this illustrative example, manufacturing environment 500 may include continuous fabrication system 502, nondestructive evaluation system 504, and cutting system 506.

As illustrated, continuous fabrication system 502 may fabricate composite structure 508. Composite structure 508 may have constant cross section 510. Composite structure 508 may have unprocessed portion 512 and processed portion 514. Unprocessed portion 512 may be comprised of raw materials processed by continuous fabrication system 502. In these illustrative examples, raw materials may be uncured materials, and continuous fabrication system 502 may be a curing system for those materials. As processed portion 514 exits continuous fabrication system 502, nondestructive evaluation system 504 is used to inspect processed portion 514. In these illustrative examples, composite structure 508 moves through continuous fabrication system 502 in the direction of arrow 516.

In this illustrative example, nondestructive evaluation system 504 may take the form of inspection array 518, which may have a plurality of transducers controlled by computer system 520.

Computer system 520 may identify shapes 522 and shapes 524 such that inconsistency 526 is substantially outside of shapes 522 and 524. Computer system 520 may control cutting machine 527 in cutting system 506 to cut processed portion 514 of composite structure 508 to form composite parts 528 and 530. In these illustrative examples, cutting machine 527 may be, for example, without limitation, a laser cutter.

In this illustrative example, composite parts 528 and 530 may be cut as processed portion 514 exits continuous fabrication system 502 after being evaluated by nondestructive evaluation system 504.

In other advantageous embodiments, a section, such as section 532, may be cut from processed portion 514. With this type of implementation, cutting machine 527 may be, without limitation, a circular saw cutting machine, a laser cutter, or some other suitable cutting machine capable of cutting processed portion 514 into sections, such as section 532.

In this illustrative example, cutting machine 527 in cutting system 506 may perform cuts around shapes 522 and 524 to fabricate parts 540 and 542 in section 544 in a manner in which inconsistency 546 may remain at least substantially outside of parts 540 and 542.

Turning now to FIG. 6, a flowchart of a process for processing a structure is depicted in accordance with an advantageous embodiment. The process illustrated in FIG. 6 may be implemented in an environment, such as manufacturing environment 300 in FIG. 3. This process may be part of a manufacturing process. For example, the process in FIG. 6 may be implemented as part of aircraft manufacturing and service method 100 as shown in FIG. 1.

The process may begin by moving processed portion 318 of composite structure 314 past nondestructive evaluation system 306 (operation 600). The process may inspect processed portion 318 of composite structure 314 for inconsistency 322 (operation 602).

In response to identifying inconsistency 322, information 328 may be generated about location 330 for inconsistency 322 in processed portion 318 of composite structure 314 using nondestructive evaluation system 306 (operation 604). Information 328 also may include, for example, without limitation, a size and/or shape for inconsistency 322.

Number of parts 302 may be cut out of processed portion 318 of composite structure 314 using cutting system 308 with information 328 from nondestructive evaluation system 306 such that inconsistency 322 may be at least substantially excluded from the composite material in number of parts 302 (operation 606), with the process terminating thereafter. In these illustrative examples, "at least substantially excluded" means that all of inconsistency 322 is excluded from the composite material in number of parts 302 or inconsistency 322 is substantially excluded from the composite material in number of parts 302.

The flowcharts and block diagrams in the different depicted embodiments illustrate the architecture, functionality, and operation of some possible implementations of apparatus and methods in different advantageous embodiments. In this regard, each block in the flowcharts or block diagrams may represent a module, a segment, a function, and/or a portion of an operation or step.

In some alternative implementations, the function or functions noted in the blocks may occur out of the order noted in the figures. For example, in some cases, two blocks shown in succession may be executed substantially concurrently, or the blocks may sometimes be executed in the reverse order, depending upon the functionality involved.

Thus, the different advantageous embodiments provide a method and apparatus for manufacturing parts from a structure. The different advantageous embodiments may include a nondestructive evaluation system configured to inspect a processed portion of a structure to determine whether an inconsistency is present in the processed portion, identify a presence of an inconsistency in the processed portion of the structure, and generate information about a location, size, and/or shape of the inconsistency in response to identifying the presence of the inconsistency. Further, the apparatus also may include a cutting system that may be configured to cut a number of parts out of the processed portion of the structure in which the inconsistency may be excluded and/or substantially excluded from the number of parts.

The different advantageous embodiments can take the form of an entirely hardware embodiment, an entirely software embodiment, or an embodiment containing both hardware and software elements. Some embodiments are implemented in software, which includes, but is not limited to, forms such as, for example, firmware, resident software, and microcode.

Furthermore, the different embodiments can take the form of a computer program product accessible from a computer-usable or computer-readable medium providing program code for use by, or in connection with, a computer or any device or system that executes instructions. For the purposes of this disclosure, a computer-usable or computer-readable medium can generally be any tangible apparatus that can contain, store, communicate, propagate, or transport the program for use by, or in connection with, the instruction execution system, apparatus, or device.

The computer-usable or computer-readable medium can be, for example, without limitation, an electronic, magnetic, optical, electromagnetic, infrared, or semiconductor system, or a propagation medium. Non-limiting examples of a computer-readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer-usable or computer-readable medium may contain or store a computer-readable or usable program code such that when the computer-readable or usable program code is executed on a computer, the execution of this computer-readable or usable program code causes the computer to transmit another computer-readable or usable program code over a communications link. This communications link may use a medium that is, for example, without limitation, physical or wireless.

A data processing system suitable for storing and/or executing computer-readable or computer-usable program code will include one or more processors coupled directly or indirectly to memory elements through a communications fabric, such as a system bus. The memory elements may include local memory employed during actual execution of the program code, bulk storage, and cache memories, which provide temporary storage of at least some computer-readable or computer-usable program code to reduce the number of times code may be retrieved from bulk storage during execution of the code.

Input/output or I/O devices can be coupled to the system either directly or through intervening input/output controllers. These devices may include, for example, without limitation, keyboards, touch screen displays, and pointing devices. Different communications adapters may also be coupled to the system to enable the data processing system to become coupled to other data processing systems or remote printers or storage devices through intervening private or public networks. Non-limiting examples are modems and network adapters and are just a few of the currently available types of communications adapters.

The description of the different advantageous embodiments has been presented for purposes of illustration and description, and it is not intended to be exhaustive or limited to the embodiments in the form disclosed. Many modifications and variations will be apparent to those of ordinary skill in the art. Although the different advantageous embodiments have been described with respect to aircraft, other advantageous embodiments may be applied to other types of objects.

For example, without limitation, other advantageous embodiments may be applied to a mobile platform, a stationary platform, a land-based structure, an aquatic-based structure, a space-based structure, and/or some other suitable object. More specifically, the different advantageous embodiments may be applied to, for example, without limitation, a submarine, a bus, a personnel carrier, a tank, a train, an automobile, a spacecraft, a space station, a satellite, a surface ship, a power plant, a dam, a manufacturing facility, a building, and/or some other suitable object.

Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
a nondestructive evaluation system configured to inspect a processed portion of a structure, determine whether an inconsistency is present in the processed portion, and generate information about a size, shape, and location of the inconsistency in a first format;
a transformation system configured to transform the information about the size, shape, and location of the inconsistency in a first format into a second format;
a cutting system configured to cut a number of parts out of the processed portion of the structure, using the information in the second format, in which the inconsistency is at least substantially excluded from the number of parts; and
a control system configured to control the cutting system, the control system comprising a number of nesting routines that update the shape of the inconsistency.

2. The apparatus of claim 1, wherein the nondestructive evaluation system is further configured to identify a presence of the inconsistency in the processed portion of the structure.

3. The apparatus of claim 2, wherein the nondestructive evaluation system is further configured to generate information about the location of the inconsistency in response to identifying the presence of the inconsistency.

4. The apparatus of claim 1 further comprising:
a continuous manufacturing system configured to process an unprocessed portion of the structure to form the processed portion.

5. The apparatus of claim 1, wherein the number of nesting routines in the control system comprise a number of software subroutines configured to execute on a computer system to identify a number of shapes for the number of parts to cut out of the processed portion of the structure using the information such that the inconsistency is at least substantially excluded from the number of parts.

6. The apparatus of claim 5, wherein the transformation system is configured to execute on the computer system, and the second format comprises aircraft coordinates used by the control process to identify the number of shapes for the number of parts to cut out of the processed portion of the structure using the information such that the inconsistency is at least substantially excluded from the number of parts.

7. The apparatus of claim 6 further comprising:
the computer system, wherein the computer system is distributed in at least one of the nondestructive evaluation system, the cutting system, and a stand alone computer.

8. The apparatus of claim 6, wherein the control system is configured to identify the number of shapes using a model in the second format for the number of parts and receive the information in the second format, and to maximize the number of parts that may be cut out of a processed portion.

9. The apparatus claim 8, wherein the model is a first computer-aided design model and wherein the information in the second format is in a second computer-aided design model.

10. The apparatus of claim 1, wherein the structure is a composite structure.

11. The apparatus of claim 1, wherein the nondestructive evaluation system is an ultrasound system.

12. The apparatus of claim 1, wherein the cutting system comprises at least one of a laser cutter and a circular blade.

13. The apparatus of claim 1, wherein the number of parts are for use in an object selected from one of a mobile platform, a stationary platform, a land-based structure, an aquatic-based structure, a space-based structure, an aircraft, a surface ship, a tank, a personnel carrier, a train, a spacecraft, a space station, a satellite, a submarine, an automobile, a power plant, a bridge, a dam, a manufacturing facility, and a building.

14. An aircraft part manufacturing apparatus comprising:
a continuous manufacturing system configured to process an unprocessed portion of a composite structure to form a processed portion of the composite structure having a continuous cross section;
a nondestructive evaluation system configured to inspect the processed portion of the composite structure, determine whether an inconsistency is present in the processed portion, identify a presence of the inconsistency in the processed portion of the composite structure, and generate information about a size, shape, and location of the inconsistency in response to identifying the presence of the inconsistency, wherein the nondestructive evaluation system is an ultrasound system;
a cutting system configured to cut a number of aircraft parts out of the processed portion of the composite structure in which the inconsistency is at least substantially excluded from the number of aircraft parts using a second format, wherein the cutting system comprises at least one of a laser cutter and a circular blade;
a computer system configured to control the nondestructive evaluation system and the cutting system;
a transformation process configured to execute on the computer system, and transform the information from a first format generated by the nondestructive evaluation system into the second format of aircraft coordinates used by a control process to identify a number of shapes for the number of aircraft parts to cut out of the processed portion of the composite structure using the information such that the inconsistency is at least substantially excluded from the number of aircraft parts; and
the control process configured to execute on the computer system to identify the number of shapes for the number of aircraft parts to cut out of the processed portion of the composite structure using a first computer-aided design model in the second format for the number of aircraft parts and the information in the second format such that the inconsistency is at least substantially excluded from the number of aircraft parts, wherein the control process is configured to identify the number of shapes using a model in the second format for the number of aircraft parts and receive the information in the second format, the control system comprising a number of nesting routines that update the number of shapes based on the information received from the evaluation system.

15. The aircraft part manufacturing apparatus of claim 14, wherein the computer system is distributed in at least one of the continuous manufacturing system, the nondestructive evaluation system, the cutting system, and a stand alone computer.

16. A method for processing a composite structure, the method comprising:
moving a processed portion of the composite structure past a nondestructive evaluation system;
inspecting the processed portion of the composite structure for an inconsistency;
identifying the inconsistency;
generating information about a size, shape, and location of the inconsistency in the processed portion of the composite structure using the nondestructive evaluation system in a first format;
transforming the information about the location of the inconsistency in a first format into a second format;
cutting at least one part out of the processed portion of the composite structure using a cutting system with the information from the nondestructive evaluation system in the second format, wherein the inconsistency is at least substantially excluded from the composite structure in the number of parts; and
controlling the cutting with a control system comprising a number of nesting routines configured to continuously update the shape of the inconsistency.

17. The method of claim 16 further comprising:
processing an unprocessed portion of the composite structure while the processed portion is being inspected.

18. The method of claim 16, wherein the cutting step comprises:
cutting the number of parts out of the processed portion of the composite structure using the cutting system with the information from the nondestructive evaluation system such that the inconsistency is at least substantially excluded from the number of parts, wherein the cutting occurs in the processed portion while the unprocessed portion of the composite structure is being processed.

19. The method of claim 16, wherein the information about the location of the inconsistency in the processed portion of the composite structure is stored in a file having a format used for a model of the number of parts.

20. The method of claim 19, wherein the cutting step comprises:
identifying a number of shapes on the processed portion of the composite structure using the model of the number of parts and the file such that the inconsistency is at least substantially outside of a perimeter for the number of shapes; and
cutting the number of parts using the number of shapes identified on the processed portion of the composite structure, wherein the inconsistency is at least substantially excluded from the composite structure in the number of parts.

21. The method of claim 16, wherein the cutting is performed using at least one of a laser and a circular blade.

22. The method of claim 16, wherein the composite structure comprises a first fiberglass sheet, a second fiberglass sheet and a core between the first fiberglass sheet and the second fiberglass sheet.

23. The method of claim 16, wherein number of parts is for use in an object selected from one of a mobile platform, a stationary platform, a land-based structure, an aquatic-based structure, a space-based structure, an aircraft, a surface ship, a tank, a personnel carrier, a train, a spacecraft, a space station, a satellite, a submarine, an automobile, a power plant, a bridge, a dam, a manufacturing facility, and a building.

24. A method for manufacturing aircraft parts, the method comprising:
manufacturing a composite structure, wherein the composite structure has an unprocessed portion and a processed portion;
moving the processed portion of the composite structure past a nondestructive evaluation system;
inspecting the processed portion of the composite structure for an inconsistency;
responsive to identifying the inconsistency, generating information about a location for the inconsistency in the processed portion of the composite structure using the nondestructive evaluation system;
transforming the information about the a size, shape, and location of the inconsistency in a first format into a second format, the second format comprising aircraft coordinates, wherein the information about the location of the inconsistency in the processed portion of the composite structure is stored in a file having a second format used for a model of a number of parts;

identifying a number of shapes on the processed portion of the composite structure using the model of the number of parts and the file such that the inconsistency is at least substantially outside a perimeter of the number of shapes;

cutting the number of parts using the number of shapes identified on the processed portion of the composite structure, wherein the inconsistency is at least substantially excluded from the composite structure in the number of parts, wherein the cutting occurs while the unprocessed portion of the composite structure is being processed; and controlling the cutting with a control system comprising a number of nesting routines configured to continuously update the shape of the inconsistency.

* * * * *